US006303127B1

(12) United States Patent
McMichael et al.

(10) Patent No.: US 6,303,127 B1
(45) Date of Patent: *Oct. 16, 2001

(54) TREATMENT OF DISEASE STATES

(75) Inventors: John McMichael, Delanson, NY (US); Harry C. Gurney, Conifer, CO (US)

(73) Assignee: Milkhaus Laboratory, Inc., Delanson, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/132,353

(22) Filed: Aug. 11, 1998

Related U.S. Application Data

(63) Continuation-in-part of application No. 08/810,725, filed on Mar. 4, 1997, now Pat. No. 5,798,102.

(51) Int. Cl.$^7$ ............................ A61K 38/16; A61K 38/48; A61K 38/27

(52) U.S. Cl. .......................... 424/198.1; 424/94.1; 514/8; 514/21

(58) Field of Search ................................ 424/198.1, 94.1; 514/8, 21

(56) References Cited

U.S. PATENT DOCUMENTS

| | | | |
|---|---|---|---|
| 4,294,818 | 10/1981 | McMichael et al. | 424/12 |
| 4,521,405 | 6/1985 | McMichael et al. | 434/92 |
| 4,666,829 | 5/1987 | Glenner et al. | 435/6 |
| 4,704,273 | 11/1987 | McMichael | 434/85 |
| 4,705,685 | 11/1987 | McMichael | 424/89 |
| 4,816,416 | 3/1989 | Averback | 436/166 |
| 4,880,626 | 11/1989 | McMichael | 424/88 |
| 4,912,206 | 3/1990 | Goldgaber et al. | 536/27 |
| 5,187,153 | 2/1993 | Cordell et al. | 514/12 |
| 5,223,482 | 6/1993 | Schilling, Jr. et al. | 514/12 |
| 5,276,059 | 1/1994 | Caughey | 514/647 |
| 5,576,289 | 11/1996 | McMichael | 514/2 |
| 5,753,624 | 5/1998 | McMichael et al. | 514/12 |
| 5,798,102 | 8/1998 | McMichael et al. | 424/198.1 |

FOREIGN PATENT DOCUMENTS

| | | |
|---|---|---|
| WO 88/03951 | 6/1988 | (WO) . |
| WO 90/14841 | 12/1990 | (WO) . |
| WO 91/16819 | 11/1991 | (WO) . |
| WO 95/31996 | 11/1995 | (WO) . |
| WO 98/05350 | 8/1997 | (WO) . |
| WO 98/39023 | 9/1998 | (WO) . |

OTHER PUBLICATIONS

Allen, A.D., "Is RA27/3 Rubella Immunization a Cause of Chronic Fatigue?", *Medical Hypotheses,* 27:217–220 (1988).

Allsop, D. et al., "Immunohistochemical Evidence For the Derivation of a Peptide Ligand from the Amyloid Beta–P-rotein Precursor of Alzheimer Disease," *Proc. Natl., Acad. Sci., USA,* 85(8):2790–2794 (Apr., 1988).

Anderton, B.H. et al., "Monoclonal antibodies show that neurofibrillary tangles and neurofilaments share antigenic determinants," *Nature,* 298:84–86 (Jul. 1, 1982).

Bahmanyar, S. et al., "Serum Antibodies to Neurofilament Antigens in Patients with Neurological and Other Diseases and in Health Controls," *J. Neuroimmunol.,* 5:191–196 (1983).

Bahmanyar, S. et al., "Characterization of Antineurofilament Autoantibodies in Creutzfeld–Jakob Disease," *J. Neuropathol. Exp. Neurol.,* 43(4):369–375 (Jul. 1984).

Bahmanyar, S. et al., "Amyloid Plaques in Spongiform Encephalopathy of Mule Deer," *J. Comp. Path.,* 95:1–5 (1985).

DeFeudis, F.V., "Beta–Amyloid Protein in Transgenic Mice," *DN&P,* 4(10):617–619 (Dec., 1991).

Elizan, T.S. et al., "Antineurofilament Antibodies in Postencephalitic and Idiopathic Parkinson's Disease," *J. Neurol. Sci.,* 59:341–347 (1983).

Fazio et al., "A preliminary study of growth hormone in the treatment of dilated cardiomyopathy," *The New England Journal of Medicine,* 334(13): 811–814 (1996).

Fazio et al., "Growth hormone in the treatment of dilated cardiomyopathy," *The New England Journal of Medicine,* 335(9):672–674 (1996).

Fessel, W.J. et al., "Abnormal Leukocytes in Schizophrenia," *Arch. Gen. Psychiatry,* 9:601–613 (1963).

Gajdusek, D.C. "Hypothesis: Interference with Axonal Transport of Neurofilament as a Common Pathogenic Mechanism in Certain Diseases of the Central Nervous System," *New Eng. J. Med.,* 312(11):714–719 (Mar. 14, 1985).

Ghiso, J. et al., "Alzheimer's Disease Amyloid Precursor Protein is Present in Senile Plaques and Cerebrospinal Fluid: Immunohistochemical and Biochemical Characterization," *Biochem. Biophys. Res. Com.,* 163(1):430–437 (Aug. 30, 1989).

Glenner, G.G., "Alzheimer's Disease The Commonest Form of Amyloidosis," *Arch. Pathol. Lab. Med.,* 107:281–282 (Jun. 1983).

Glenner, G.G. et al., "Alzheimer's Disease and Down's Syndrome: Sharing of a Unique Cerebrovascular Amyloid Fibril Protein," *Biochem. Biophys. Res. Com.,* 122(3):1131–1135 (1984).

Goldgaber, D. et al., "Characterization and Chromosomal Localization of a cDNA Encoding Brain Amyloid of Alzheimer's Disease," *Science,* 235:877–880 (Feb., 1987).

(List continued on next page.)

Primary Examiner—Geetha P. Bansal
(74) *Attorney, Agent, or Firm*—Marshall, Gerstein & Borun

(57) ABSTRACT

The invention presents methods for the treatment of symptoms associated with diseases states including cardiomyopathy, Parkinson's Disease and degenerative liver disease including cirrhosis comprising treatment with an effective amount of a composition comprising beta-amyloid, streptolysin O, and growth hormone.

7 Claims, No Drawings

OTHER PUBLICATIONS

Goldman, R.D. et al., "Cytoplasmic Fibers in Mammalian Cells: Cytoskeletal and Contractile Elements," *Ann. Rev. Physiol.*, 41:703–722 (1979).

Griffin, J.W. et al., "Slow Axonal Transport of Neurofilament Proteins: Impairment by $\beta,\beta'$–Iminodipropionitrile Administration," *Science*, 202:633–635 (Nov. 1978).

Gupta, S. et al., "Effect of Intraventricular Administration of Streptolysin O on the Electrocardiogram of Dogs," *Toxicon*, 18:389–391 (1980).

Hoffman, P.N. et al., "The Slow Component of Axonal Transport," *J. Cell Biol.*, 66:351–366 (1975).

Howard, J. et al., "Antibodies to fibronectin bind plaques and other structures in Alzheimer's disease and control brain," *Neuroscience Letters*, 118:71–76 (1990).

Iqbal, K. et al., "Chemical Relationship of the Paired Helical Filaments of Alzheimer's Dementia to Normal Human Neurofilaments and Neurotubules," *Brain Res.*, 142:321–332 (1978).

Itagaki, S. et al., "Presence of T–Cytotoxic Suppressor and Leucocyte Common Antigen Positive Cells in Alzheimer's Disease Brain Tissue," *Neuroscience Letters*, 91:259–264 (1988).

Joachim, C.L. et al., "Amyloid Protein in Alzheimer's Disease," *J. Gerontology*, 44:(4):B77–84 (1989).

Jones, J.F. et al., "Evidence for Active Epstein–Barr Virus Infection in Patients with Persistent, Unexplained Illnesses: Elevated Anti–Early Antigen Antibodies," *Annals of Internal Medicine*, 102:1–6 (Jan. 1985).

Kang, J. et al., "The precursor of Alzheimer's disease amyloid A4 protein resembles a cell–surface receptor," *Nature*, 325:733–736 (Feb. 19, 1987).

Kilbourne, E.D. "Inactivated Influenza Virus Vaccines" in *Vaccines*, pp. 420–434, Plotkin et al., Eds., W.B. Saunders Company, Philadelphia (1988).

Knight, J.G., "Dopamine–Receptor–Stimulating Autoantibodies: A Possible Cause of Schizophrenia," *Lancet*, 82:1073–1076 (Nov. 13, 1982).

Komaroff, A.L., "The 'Chronic Mononucleosis' Syndromes," *Hospital Practice*, 71–75 (May 30, 1987).

Lasak, R.J., "The Dynamic Ordering of Neuronal Cytoskeletons," *Neurosciences. Res. Prog. Bull.*, 19(1):7–32 (1981).

Lieberman, A.D., "The Role of the Rubella Virus In the Chronic Fatigue Syndrome," *Clinical Ecology*, 7(3):51–54 (1990).

Loh, E. et al., "Growth hormone for heart failure—Cause for cautious optimism," *The New England Journal of Medicine*, 334:No. 13, 856–857 (1996).

Ma J., et al., "Amyloid–associated proteins $\alpha_1$ antichymotrypsin and apolopoprotein E promote assembly of Alzheimer $\beta$–protein into filaments," *Nature*, 372:92–94 (Nov. 3, 1994).

Marx, J., "Alzheimer's Debate Biols Over," *Science* 257:1336–1338 (Sep. 4, 1992).

Marx, J., "Testing of Autoimmune Therapy Begins," *Science*, 252:27–28 (Apr. 5, 1991).

Marx, J., "A New Link in the Brain's Defenses," *Science*, 256:1278–1280 (May 29, 1992).

Masters, C.L. et al., "Amyloid plaque core protein in Alzheimer disease and Down syndrome," *Proc. Natl. Acad. Sci. USA*, 82:4245–4249 (Jun. 1985).

Melnick, J.L. et al., "Possible Role of Cytomegalovirus in Atherogenesis," *JAMA*, 263(16):2204–207 (Apr. 25, 1990).

Miller, J.A., "Food Allergy: Technique of Intradermal Testing & Subcutaneous Injection Therapy," *Transactions of the American Society of Ophthalmologic and Otolaryngologic Allergy*, vol. 16(1):154–168 (Oct. 1976).

Miller, J.B., "A Double–Blind Study of Food Extract Injection Therapy: A Preliminary Report," *Annals of Allergy*, 38:185–191 (Mar. 1977).

Miller, J.B., "Influenza: Rapid Relief Without Drugs," *Clinical Medicine*, 81:16–19 (Sep. 1974).

Miller, J.B., "Influenza and Herpes Treatment and Responses", *Relief at Last: Neutralization for Food Allergy and Other Illnesses* Ch. 27, 239–248 (1987).

Miller, J.B., "The Importance of Herpes Virus Infections and the Ability to Neutralize Them", *Relief at Last: Neutralization for Food Allergy and Other illnesses* Ch. 29, 256–263 (1987).

Miller, J.B., "Treatment of Active Herpes Virus Infections with Influenza Virus Vaccine", *Annals of Allergy*, 42:295–305 (1979).

Moos, R.H. et al., "Psychologic Comparisons Between Women with Rheumatoid Arthritis and Their Nonarthritic Sisters," *Psychosom. Med.*, 27(2):135–149 (1965).

Newcombe, D.S. et al., "Solubility Characteristics of Isolated Amyloid Fibrils," *Biochem. et Biophys. Acta*, 104:480–486 (1965).

Pennish, E., "A Molecular Whodunit New Twists in the Alzheimer's Mystery," *Science News*, 145:8–11 (Jan. 1, 1994).

Rabins, P.V. et al., "The Dementia Patient: Evaluation and Care," *Geriatrics*, 38(8):99–117 (Aug. 1983).

Razin, E. et al., "Protein Kinases C–$\beta$ and C–$\epsilon$ link the mast cell high–affinity receptor for IgE to the expression of c–fos and c–jun," *Proc. Nat'l. Acad. Sci. (USA1)*, 91:7722–7726 (1994).

Reines, S.A., "Early Clinical Trials in Alzheimer's Disease: Selection and Evaluation of Drug Candidates," *Progress in Clin. Biol. Res.*, 1283–1290 (1989).

Samet, M.K., Peptides Offer Promise for Treating Alzheimer's and other Neurodiseases, *Genetic Engineering News*, p. 24 (Jul./Aug. 1991).

Selkoe, D.J., "In the beginning . . . " *Nature*, 354:432–433 (Dec. 12, 1991).

Selkoe, D.J. et al., "Isolation of Low–Molecular–Weight Proteins from Amyloid Plaque Fibers in Alzheimer's Disease," *J. Neurochem.*, 46:1820–1834 (1986).

Selkoe, D.J. et al., "Isolation of Paired Helical Filaments and Amyloid Fibers from Human Brain," *Methods in Immunology*, 134:388–404 (1986).

Shacks, S.J. et al., "Increased Serum IgG4 Levels in Acute Epstein–Barr Viral Mononucleosis," *Annals of Allergy*, 54:284–288 (Apr. 1985).

Shelanski, M.L. et al., "Introduction." *Neurosci Res Program Bull*, 19(1):5–6 (1981).

Shelanski, M.L. et al., "Neurofilaments," *J. Neurochem.*, 33:5–13 (1979).

Snow, A.D. et al., "Proteoglycans in the Pathogenesis of Alzheimer's Disease and Other Amyloidoses," *Neurobio. Aging.*, 10:481–497 (1989).

Solomon, G.F., "Psychoneuroimmunology: Interactions Between Central Nervous System and Immune System," *J. Neurosci. Res.*, 18:1–9 (1987).

Solomon, G.F. et al., "Emotions, Immunity, and Disease," *Arch. Gen. Psychiatry*, 11:657–674 (Dec. 1964).

Strauss, S.E. et al., "Persisting Illness and Fatigue in Adults with Evidence of Epstein–Barr Virus Infection," *Annals of Internal Medicine,* 102:7–16 (1985).

Tanzi, R.E. et al., "Amyloid β Protein Gene: cDNA, mRNA Distribution, and Genetic Linkage Near the Alzheimer Locus," *Science,* 235:880–884 (Feb. 20, 1987).

Tingle, A.J. et al., "Prospective Immunological Assessment of Arthritis Induced by Rubella Vaccine," *Infect. Immun.,* 40(1):22–28 (Apr. 1983).

Toh, B.H. et al., "The 200– and 150–kDa neurofilament proteins react with IgG autoantibodies from patients with kru, Creutzfeldt–Jakob disease, and other neurologic diseases," *Proc. Natl. Acad. Sci., USA,* 82(10):3485–3489 (1985).

Turnell, W. et al., "Secondary Structure Prediction of Human $SAA_1$ Presumptive Identification of Calcium and Lipid Binding Sites," *Mol. Biol. Med.,* 3:387–407 (1986).

Turnell, W. et al., "X–Ray Scattering and Diffraction by Wet Gels of AA Amyloid Fibrils," *Mol. Biol. Med.,* 3:409–424 (1986).

Whitson, J. et al., "Amyloid Beta Protein Enhances the Survival of Hippocampal Neurons in Vitro," *Science,* 243:1488–1490 (Mar. 17, 1989).

Wirak, D.O. et al., "Deposits of Amyloid β Protein in the Central Nervous System of Transgenic Mice," *Science,* 253:323–325 (Jul. 19, 1991).

Wong, C.W. et al., "Neuritic plaques and cerebrovascular amyloid in Alzheimer disease are antigenically related," *Proc. Natl. Acad. Sci. USA,* 82:8729–8732 (Dec. 1985).

Yanker, B.A. et al., "Neurotrophic and Neurotoxic Effects of Amyloid β Protein: Reversal by Tachykinin Neuropeptides," *Science,* 250:279–282 (Oct. 12, 1990).

Zurawaki, G. et al., "Activation of Mouse T–Helper Cells Induces Abundant Preproenkephalin mRNA Synthesis," *Science,* 232:772–775 (May 9, 1986).

Narula, J. et al., "Does Endomyocardial Biopsy Aid in the Diagnosis of Active Rheumatic Carditis?" *Circulation,* 88[part 1]:2198–2205 (1993).

TREATMENT OF DISEASE STATES

This is a continuation-in-part of U.S. Ser. No. 08/810,725 filed Mar. 4, 1997 (U.S. Pat. No. 5,798,102).

FIELD OF INVENTION

This invention relates generally to methods and materials for the treatment and amelioration of the symptoms associated with cardiomyopathy in non-human animals, Parkinson's Disease, and degenerative liver disease including cirrhosis.

BACKGROUND OF THE INVENTION

Cardiomyopathy is a disease of the heart muscle. This form of heart disease is often distinctive, both in general symptoms and in patterns of blood flow, to allow a diagnosis to be made. Increasing recognition of this disease, along with improved diagnostic techniques, has shown that cardiomyopathy is a major cause of morbidity and mortality. In some areas of the world it may account for as many as 30 percent of all deaths due to heart disease.

Cardiomyopathy can result from a variety of structural or functional abnormalities of the ventricular myocardium. A large number of cardiomyopathies are apparently not related to an infectious process and are not well understood. Some are congenital and may cause enlargement of the heart. Metabolic diseases associated with endocrine disorders may also cause cardiomyopathies. Infections, such as acute rheumatic fever and several viral infections, may cause a number of types of myocarditis. Myocarditis may also occur as a manifestation of a generalized hypersensitivity reaction, allergic or immunologic. The heart may also be affected by any of a considerable number of collagen diseases. Collagen is the principal connective tissue protein, and collagen diseases are diseases of the connective tissues. They include diseases primarily of the joints, skin, and systemic disease.

There are three clinical classifications of cardiomyopathy; hypertrophic, restrictive, and dilated congestive. Dilated congestive cardiomyopathy is a disorder of myocardial function where ventricular dilation occurs, often following virus infection. Restrictive cardiomyopathy occurs as a consequence of the ventricular walls becoming rigid so that the chambers are unable to fill adequately. This is usually idiopathic. Hypertrophic cardiomyopathy is characterized by ventricular hypertrophy and may be congenital or acquired. The prognosis for all three types of disease is guarded at best and often poor. Treatment of cardiomyopathy involves restricted activity, stress avoidance, treatment with beta-blockers, prophylactic antibiotic therapy, use of anti-coagulants, calcium channel blockers, surgery, and cardiac transplantation.

Of interest to the present application are the disclosure of co-owned published PCT international applications PCT/US91/01898 published Nov. 14, 1991, PCT/US95/06689 published Nov. 30, 1995, and PCT/US97/14005 filed Aug. 8, 1997 and U.S. Pat. No. 5,753,624 issued May 19, 1998 the disclosures of which are hereby incorporated by reference. These references relate in part to methods for alleviating symptoms associated with amyloid plaque formation and/or formation of arterial plaques comprising the step of administering to a patient an effective amount of amyloid protein.

Recent literature reports have focused on the use of somatotropin, a growth hormone, for the treatment of cardiomyopathy. See: "A Preliminary Study of Growth Hormone in the Treatment of Dilated Cardiomyopathy, "*N.E. J. of Medicine*, 334(13), pp. 811–814 (1996). However, cautionary responses to such reports speak to the possibility, or even likelihood, of inducing cancer, arrhythmias, and other problems with growth hormone therapy using the concentrations now being evaluated by those authors. Accordingly, there remains a desire in the art for effective cardiomyopathy therapies that allow reduction in the amount of growth hormone administered and do not suffer from the limitations of the prior methods.

SUMMARY OF THE INVENTION

The present invention relates to the discovery that treatment of cardiomyopathy with a combination of compounds is effective in improving heart function. The therapeutic composition described herein is comprised of three compounds, each with a specific function relative to the amelioration of symptoms associated with cardiomyopathy. They are: beta-amyloid protein, streptolysin O, and growth hormone. It has been found that the administration of these compounds in combination is surprisingly effective in treating the symptoms associated with cardiomyopathy and allows a reduction in the amount of growth hormone required for a useful therapeutic effect.

Beta-amyloid acts to reduce vascular plaquing that may be associated with the disease. Streptolysin O reduces or eliminates cardiac scarring associated with the heart disease. Streptolysin O is one of a group of filterable hemolysins derived from Group A beta-hemolytic streptococci. Specifically, streptolysin O is a 60kD peptide which is hemolytic in its reduced state but is inactivated upon oxidation. Streptolysin O is used in the art generally as an analytical reagent for permeabilizing cells. See, e.g., Razin et al., *Proc. Nat'l. Acad. Sci. (USA)*, 91:7722–7726 (1994). Co-owned U.S. Pat. No. 5,576,289, the disclosure of which is incorporated by reference, discloses the use of streptolysin O in methods for treating disease states characterized by motor deficit disorders. No disclosure is made in that patent of utility of streptolysin O in treating cardiomyopathy.

Growth hormone stimulates healing of the compromised heart. Growth hormone functions to regulate somatic growth and also maintains muscle mass and strength. It can also act as a counterregulatory hormone opposing the action of insulin on carbohydrate and lipid metabolism.

It has been discovered that by administration of a combination of the above compounds symptoms associated with cardiomyopathy are reduced or stabilized. The present invention provides methods for treating cardiomyopathy by administration of an effective amount of a composition comprising beta-amyloid, streptolysin O, and growth hormone. Methods of the invention result in amelioration of the symptoms associated with cardiomyopathy such as angina, fatigue, loss of strength, respiratory insufficiency, edema, interrupted sleep, recurrent respiratory infection, and the like. Noticeable improvement and/or stabilization of the disease symptoms were obtained after treatment. Improved Ejection Fraction (EF), blood pressure, and echo cardiogram readings were also noted in some cases.

The invention comprises the step of administering an effective amount of beta-amyloid, streptolysin O, and growth hormone in combination, to a human or non-human subject suffering from cardiomyopathy. The precise dose will vary among patients and may readily be determined by those skilled in the art. Useful dosages generally range from about $1 \times 10^{-11}$ mg to 10 mg of beta-amyloid, about 0.0005 units to 50 units streptolysin O, and about $1 \times 10^{-16}$ I.U. to 100 I.U. growth hormone, with preferred dosages of from about $10^{-7}$ mg to 1.0 mg, 0.1 units to 10 units, and $10^{-4}$ I.U.

to 10 I.U., of each compound respectively. It is particularly preferred that dosages of about 0.1 I.U. or less of growth hormone be used to minimize potential negative effects of growth hormone therapy. Most preferred is the use of growth hormone at dosages of 0.01 I.U. or less. The compositions of the invention may be administered by a variety of routes of administration including intravenous, intramuscular, subcutaneous, intrathecal, and oral, with sublingual administration being preferred. It is also anticipated that alternative routes of administration may be by inhalation and topical application.

The preferred dosage for sublingual application is 1–10 drops (0.05 ml/drop) per day according to the above formula. Subcutaneous injections are administered 1–3 times a day.

The invention further provides Parkinson's Disease in a subject, comprising the step of administering to a subject diagnosed with Parkinson's Disease a composition comprising an effective amount of beta-amyloid, streptolysin O, and growth hormone. The precise dose will vary among patients and may readily be determined by those skilled in the art. Useful dosages generally range from about $1 \times 10^{-11}$ mg to 10 mg of beta-amyloid, about 0.0005 units to 50 units streptolysin O, and about $1 \times 10^{-16}$ I.U. to 100 I.U. growth hormone, with preferred dosages of from about $10^{-7}$ mg to 1.0 mg, 0.1 units to 10 units, and $10^{-4}$ I.U. to 10 I.U., of each compound respectively. It is particularly preferred that dosages of about 0.1 I.U. or less of growth hormone be used to minimize potential negative effects of growth hormone therapy. Most preferred is the use of growth hormone at dosages of 0.01 I.U. or less. The compositions of the invention may be administered by a variety of routes of administration including intravenous, intramuscular, subcutaneous, intrathecal, and oral, with sublingual administration being preferred. It is also anticipated that alternative routes of administration may be by inhalation and topical application.

The preferred dosage for sublingual application is 1–10 drops (0.05 ml/drop) per day according to the above formula. Subcutaneous injections are administered 1–3 times a day.

The invention further provides degenerative liver disease in a subject, comprising the step of administering to a subject diagnosed with degenerative liver disease a composition comprising an effective amount of beta-amyloid, streptolysin O, and growth hormone. Degenerative liver diseases which may be treated according to the invention include, but are not limited to cirrhosis. The precise dose will vary among patients and may readily be determined by those skilled in the art. Useful dosages generally range from about $1 \times 10^{-11}$ mg to 10 mg of beta-amyloid, about 0.0005 units to 50 units streptolysin O, and about $1 \times 10^{-16}$ I.U. to 100 I.U. growth hormone, with preferred dosages of from about $10^{-7}$ mg to 1.0 mg, 0.1 units to 10 units, and $10^{-4}$ I.U. to 10 I.U., of each compound respectively. It is particularly preferred that dosages of about 0.1 I.U. or less of growth hormone be used to minimize potential negative effects of growth hormone therapy. Most preferred is the use of growth hormone at dosages of 0.01 I.U. or less. The compositions of the invention may be administered by a variety of routes of administration including intravenous, intramuscular, subcutaneous, intrathecal, and oral, with sublingual administration being preferred. It is also anticipated that alternative routes of administration may be by inhalation and topical application.

The preferred dosage for sublingual application is 1–10 drops (0.05 ml/drop) per day according to the above formula. Subcutaneous injections are administered 1–3 times a day.

Additional aspects and advantages of the invention will become apparent upon consideration of the following detailed description thereof.

DETAILED DESCRIPTION OF THE INVENTION

It has been discovered that treatment of a patient suffering from cardiomyopathy with a composition comprising beta-amyloid, streptolysin O, and growth hormone can reduce or stabilize the disease symptoms. Administration of the composition of the invention has been shown to be effective in clinical improvement in angina, energy, and strength. It has also been shown to have a stabilizing effect on echocardiogram testing indicating improved cardial function and efficiency.

A number of animal and human clinical trials have been conducted and the results are presented herein in the form of several examples. In each human test case, clinical histories of the patients were known or taken prior to treatment according to the invention. In the reported examples, reduction or stabilization of the adverse symptoms of cardiomyopathy were noted. In some cases, improved EF ratings were observed after treatment according to the invention, along with increased energy and strength. In treatment of dogs of various breeds, ages, and sizes, disease symptoms either remained stable or improved without adverse effects. In 70% of the cases, improved performance, endurance, and vitality were observed in dogs.

Compositions according to the invention comprise effective combinations of from about $1 \times 10^{-10}$ to about $1 \times 10$ mg beta-amyloid, from about 0.0005 units to about 50 units streptolysin O, and from about $1 \times 10^{-6}$ International Units (I.U.) to about 100 I.U. growth hormone. According to a preferred embodiment, a composition is provided which comprises about $4 \times 10^{-9}$ mg beta-amyloid, about 2 units streptolysin O, and less than 4 I.U. of human growth hormone with less than 0.1 I.U. being preferred and about 0.01 I.U. growth hormone being particularly preferred. Growth hormone used in this invention can be of a human, porcine, bovine, or other source, and can be produced by recombinant methods.

Proper dosing of the composition of the present invention may easily be determined by the skilled artisan using standard procedures and upon evaluation of the severity of a patient's symptoms. The compositions of the invention may be formulated in an appropriate pharmaceutical vehicle, including water, saline, dextrose, and albumin.

In the present invention, human patients in the foregoing examples were treated using relatively low doses of the compositions. Drops were administered daily of a composition comprising $4 \times 10^{-9}$ mg beta-amyloid, 2 units streptolysin O, and 0.01 I.U. growth hormone. The preferred route of administration was sublingually and patients were generally instructed to self-administer from one to about 6 drops daily.

Provided below are case histories of patients being treated according to the invention which provide evidence of the effectiveness of the treatment methods described herein.

The following Examples are intended to illustrate practice of the preferred embodiments of the invention. Numerous additional embodiments and improvements are apparent upon consideration of the following Examples.

EXAMPLE 1

Cardiomyopathy

Forty dogs of varied ages, breeds, and exhibiting symptoms of cardiomyopathy were treated with a 0.2 cc subcutaneous injection of the composition of the invention comprising $4\times10^{-9}$ mg beta-amyloid, 2 units streptolysin O and 0.01 I.U. growth hormone. Prior to treatment, the dogs were lethargic, depressed, and easily exhausted. After treatment of several weeks to several months, the dogs exhibited noticeable improved performance and energy. Significant improved activity performance and vitality was observed in 70% of the dogs.

EXAMPLE 2

Cardiomyopathy

A 74-year-old male with a history of cardiomyopathy was treated according to the methods and compositions of the invention. The patient received 4 drops a day of a composition comprising $4\times10^{-9}$ mg beta-amyloid, 2 units streptolysin O, and 0.01 I.U. growth hormone. His initial ejection fraction (EF) by echocardiogram was 35%, while three months later it had improved to 50%. A repeat echocardiogram was not readable at the six-month evaluation, however, a MUGA (multiple gated acquisition) scan revealed a normal EF of 53%. This reading was significantly better than the baseline EF of 35%, even with the variation in echocardiogram versus MUGA EF determinations. After approximately 6 months of treatment, the patient's blood pressure was 140/70 with a heart rate of 68. One month later, his blood pressure was 122/82 with only one episode of chest pain. A significant improvement in left ventricular function was noted. The patient has reported increased energy and strength and reported no angina symptoms for one month.

EXAMPLE 3

Cardiomyopathy

A 73-year-old male with a history of multiple cardiomyopathic symptoms was treated according to the procedure set out in Example 2. His initial EF by echocardiogram was 25%, while three months after treatment, his EF was 20%. At the six-month evaluation, he had 2+edema (nonpitting) and a repeat echocardiogram revealed an EF of 25–30% compared to a baseline of 25%. The patient's blood pressure was 142/70. The patient reported dramatic clinical improvement in angina, energy, and strength. After another month of treatment, his echocardiogram EF remained unchanged, but he continued to have no angina, good energy levels, and strength. He also reported that when he stopped using the composition after 2–3 days, he had pain across his anterior chest and became more fatigued and complained of less strength.

EXAMPLE 4

Cardiomyopathy

A 70-year-old female with a history of multiple medical problems, including cardiomyopathy, was treated according to the procedure set out in Example 2. This patient had multiple admissions to the hospital with recurrent angina and congestive heart failure. Her EF remained severely depressed at 10–15% after seven months treatment. She had severe coronary artery disease and prognosis was poor. The patient had periods of improvement clinically, but this was earlier in treatment according to the invention. Her initial EF by echocardiogram was 15–20%, while three months later it was 10–15%. It has remained stable for an additional three months. She recently suffered another episode of angina and her EF remains at 10%. It is believed advanced coronary disease prevented a more positive response to the compositions of the invention.

EXAMPLE 5

Cardiomyopathy

An 86-year-old male with a history of a dilated cardiomyopathy and an EF of 25% by a chemical stress sestamibi prior to treatment according to the invention. He also had moderately severe chronic obstructive pulmonary disease (COPD). His main symptoms include dyspnea and palpitations, especially during exertion, extreme fatigue, lethargy, and shortness of breath. After one month of treatment with 1 drop of a composition, according to Example 2, four times daily, his blood pressure was 142/80 and his lungs were clear but decreased. His pulse was 72.

After two months of treatment, he was slightly improved and continued to have less severe dyspnea and less lethargy. He continued to be fatigued, but needed less sleep. Palpitations were present, but less frequent. His energy level was similar, although he was more active. There appeared to be slight clinical improvement overall after two months of treatment according to the therapy.

EXAMPLE 6

Cardiomyopathy

A 69-year-old male with a history of ischemic cardiomyopathy, chronic atrial fib/flutter, COPD, diabetes mellitus type 2, congestive heart failure, and hyperlipidemia was treated with 1 drop four times daily according to the procedure in Example 2. An initial echocardiogram revealed an EF of 10–20%. Prior to treatment, this patient had been a virtual invalid and practically confined to a chair. He had tachycardia intermittently, extreme fatigue, and dyspnea with minimal exertion. He also had extreme shortness of breath. On the first day of treatment, his blood pressure was 102/70. His lung sounds were decreased and the heart rhythm was atrial fibrillation.

A month after treatment began, he was walking without shortness of breath and his energy improved. His palpitations, which were occurring daily, had occurred only once in two weeks. He had no chest pain. He continued to improve and had no palpitations or chest pain after two months of treatment. He developed dyspnea and palpitations, however, after physical exertion using a treadmill.

After an additional two weeks of treatment, the patient continued to significantly improve. He was no longer confined to a chair and is able to walk about throughout the day. His lungs were clear, but had a trace of edema. His blood pressure remained good.

The following examples are directed to treatment of Parkinson's Disease using the compositions of the invention comprising the combination of beta-amyloid, streptolysin O, and growth hormone.

EXAMPLE 7

Parkinson's Disease

According to this example a 71 year-old female diagnosed with Parkinson's Disease had been treated with medications including Sinemet 50/200 CR BID and Permax .25 BID for three years. Her initial complaints were difficulty moving her left side, problems with handwriting and trouble with gait. Prior to treatment with the composition of the invention she continued to have a slight left tremor (upper extremity), cogwheel rigidity on the left and masked facies. Upon examination, she complained of numbness bitemporally, heavy tired feeling in the afternoon, difficulty with left arm and left leg movement, tremor with fatigue, trouble typing letters and trouble getting her words out at times. Further, she swayed with walking with arms at her sides, had mild flexion/extension weakness of her left arm and left leg and minimal to no spasticity. Neither significant cogwheel rigidity or tremor was detected.

The subject was treated with sublingual administration of a composition comprising $4 \times 10^{-9}$ mg beta-amyloid, 2 units streptolysin O, and 0.01 I.U. growth hormone three times daily. Upon follow-up examination four weeks later the subject was able to type a letter for the first time in 3 to 4 months. Previously, the subject could not coordinate the left hand with the right. Upon follow-up examination one month later the subject reported that she felt fatigued after her vacation and was unable to type since she felt tired but that there were no other changes including tremor. Her dosage was then increased to four times daily.

EXAMPLE 8

Parkinson's Disease

According to this example a 67 year-old female diagnosed with Parkinson's Disease initially declined treatment but was treated with Sinemet which helped her tremor. After one year of treatment the subject developed side effects and discontinued treatment with Sinemet although she continued treatment for other conditions including Synthroid for hypothyroid, Isoptin for hypertension, Navane (paranoia), Benadryl, Cogentin, Lescol and estrogen. Her mental state has been stable for years. Upon evaluation, three years after her original diagnosis, her complaints included upper extremity tremor at rest which caused her to spill coffee on herself, falling to the left side, fatigue and tremor in her legs while she sat in a chair. On exam, she had cogwheel rigidity, right arm greater than left arm. She had tremor at rest in her legs and cogwheeling in both legs. She had noticeable bobbing of her head.

The subject was treated with sublingual administration of a composition comprising $4 \times 10^{-9}$ mg beta-amyloid, 2 units streptolysin O, and 0.01 I.U. growth hormone three times daily. Upon follow-up examination three weeks later the subject noted complete resolution of her lower extremity tremor 2–3 days after initiating therapy according to the invention. She said she was not swaying to the side and had not fallen.

On examination, there was no change in the upper extremities, but the legs had no tremor. One month later, she still had resolution of tremor in her legs at home, but mild tremor was noted by the attending physician. She still was staggering at times. She noted a 20% decrease in hand tremor which was not obvious to the attending physician but could have been accurate given that the subject was no longer spilling coffee on herself. Her assessment could be accurate since she no longer spilled coffee on herself. No other changes were noted.

The following examples are directed to treatment of degenerative liver conditions, including cirrhosis, using the compositions of the invention comprising the combination of beta-amyloid, streptolysin O, and growth hormone.

EXAMPLE 9

Cirrhosis

According to this example, a female subject about 60 years old suffering from advanced cirrhosis and extreme physical weakness and was projected to die within two months and was sent home from the hospital to undergo hospice care. The subject was treated with sublingual administration of a composition comprising $4 \times 10^{-9}$ mg beta-amyloid, 2 units streptolysin O, and 0.01 I.U. growth hormone four times daily and began to respond favorably after three days and regained strength. The subject was treated with no other medication and continued to lead a near normal life for over two years.

EXAMPLE 10

Degenerative Liver Function

According to this example, a male subject about 45 years old suffered from degenerative liver function and placed on the waiting list for liver transplant was treated with sublingual administration of a composition comprising $4 \times 10^{-9}$ mg beta-amyloid, 2 units streptolysin O, and 0.01 I.U. growth hormone. Reports from the subject indicate that after three months of treatment with the composition of the invention all indicators of liver function had improved substantially. In particular, platelet count which had been considered critically low at between 58 and 66 K/cmm for eight years prior to treatment according to the invention had risen to about 100 K/cmm (normal is considered 172–376).

EXAMPLE 11

Degenerative Liver Function in Canines

According to this example, several old dogs exhibiting abnormal liver profiles and compromised health were treated by one subcutaneous injection daily of the composition of the invention comprising $4 \times 10^{-9}$ mg beta-amyloid, 2 units streptolysin O, and 0.01 I.U. growth hormone. The dogs responded positively to the treatment when evaluated both by performance criteria and lab results.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method for treatment of cardiomyopathy in non-human animals, comprising the step of administering to the animal diagnosed with cardiomyopathy a composition comprising an effective amount of beta-amyloid, streptolysin O, and growth hormone wherein said amount of growth hormone is from about $1 \times 10^{-6}$ to 0.1 International Units per dose.

2. The method according to claim 1 wherein said amount of beta-amyloid is from about $1 \times 10^{-11}$ mg to about 10 mg, and streptolysin O is from about 0.005 to about 50 units.

3. The method according to claim 1 wherein said amount of beta-amyloid is about $4 \times 10^{-9}$ mg streptolysin O is 2 Units, and growth hormone is 0.01 International Units.

4. The method of claim 1 wherein said growth hormone is less than or equal to 0.01 International Units.

5. The method according to claim 1 wherein said composition is administered by a method selected for the group consisting of intramuscular, sublingual, intravenous, subcutaneous, intrathecal, inhalation and topical.

6. The method of claim 5 wherein said composition is administered intravenously.

7. The method of claim 6 wherein said composition is in a pharmaceutically acceptable vehicle.

* * * * *